(12) United States Patent
Bhogal et al.

(10) Patent No.: US 7,807,707 B2
(45) Date of Patent: Oct. 5, 2010

(54) HAIR AND/OR SCALP CARE COMPOSITIONS INCORPORATING AMINO-OXO-INDOLE-YLIDENE COMPOUNDS

(75) Inventors: Ranjit Bhogal, Bedford (GB); Jasveen Chugh, Chigwell (GB); Helen Meldrum, Trumbull, CT (US)

(73) Assignee: Conopco Inc., Englewood Cliffs, NJ (US)

( * ) Notice: Subject to any disclaimer, the term of this patent is extended or adjusted under 35 U.S.C. 154(b) by 307 days.

(21) Appl. No.: 11/886,202

(22) PCT Filed: Feb. 27, 2006

(86) PCT No.: PCT/EP2006/001825
§ 371 (c)(1),
(2), (4) Date: Sep. 11, 2007

(87) PCT Pub. No.: WO2006/097193
PCT Pub. Date: Sep. 21, 2006

(65) Prior Publication Data
US 2008/0206180 A1 Aug. 28, 2008

(30) Foreign Application Priority Data
Mar. 12, 2005 (EP) .................... 05251512

(51) Int. Cl.
*A61Q 5/00* (2006.01)
*A01N 43/36* (2006.01)
*A61K 8/00* (2006.01)
*C07D 209/00* (2006.01)

(52) U.S. Cl. .............. 514/426; 548/483; 424/70.1; 424/70.22; 424/70.27

(58) Field of Classification Search .......... None
See application file for complete search history.

(56) References Cited

U.S. PATENT DOCUMENTS

| 3,694,547 | A | * | 9/1972 | Forsthoff | 424/94.66 |
|---|---|---|---|---|---|
| 5,324,737 | A | | 6/1994 | D'Ambra et al. | 514/323 |
| 5,514,672 | A | | 5/1996 | Bazzano | 514/168 |
| 5,817,651 | A | | 10/1998 | D'Ambra et al. | 514/210 |
| 6,054,450 | A | | 4/2000 | Shin et al. | 514/188 |
| 6,451,300 | B1 | | 9/2002 | Dunlop et al. | 424/70.27 |
| 6,465,421 | B1 | | 10/2002 | Duranton et al. | 514/1 |
| 7,067,153 | B2 | | 6/2006 | Grisoni | 424/490 |
| 2003/0049220 | A1 | | 3/2003 | Bailey et al. | 424/70.1 |
| 2003/0078289 | A1 | | 4/2003 | Aspnes et al. | 514/415 |
| 2003/0180277 | A1 | | 9/2003 | Hoppe et al. | 424/94.1 |
| 2003/0180278 | A1 | | 9/2003 | Hoppe et al. | 424/94.1 |
| 2004/0151682 | A1 | | 8/2004 | Biehl et al. | 424/70.13 |
| 2005/0019438 | A1 | | 1/2005 | Bourges-Sevenier et al. | 424/778 |
| 2005/0043388 | A1 | * | 2/2005 | Bombrun et al. | 514/414 |
| 2008/0255224 | A1 | | 10/2008 | Blum | 514/454 |

FOREIGN PATENT DOCUMENTS

| DE | 100 36 799 | 2/2002 |
|---|---|---|
| EP | 0 418 806 | 1/1994 |
| EP | 0 693 278 | 1/1996 |
| EP | 0 116 439 | 8/2004 |
| FR | 2 677 223 | 12/1992 |
| FR | 2 696 318 | 4/1994 |
| GB | 802 111 | 10/1958 |
| JP | 06 016531 | 1/1994 |
| JP | 10 330259 | 12/1998 |
| WO | 01/82861 | 11/2001 |
| WO | 02/09657 | 2/2002 |
| WO | 02/24319 | 3/2002 |
| WO | 02/09664 | 12/2002 |
| WO | 02/096369 | 12/2002 |
| WO | 03/007901 | 1/2003 |
| WO | 2005/004858 | 1/2005 |

OTHER PUBLICATIONS

Indian Drugs, vol. 23, issue 3, 1985, Prakash et al.*
Varma, Rajendra S., Garg, Pradeep K.; "Synthesis of 3-Arylglycylhydrazono-2-indolinones as Amoebicidal and Antibacterial Agents," 1981, Indian Pharmaceutical Association, Indian Journal of Pharmaceutical Sciences, vol. 43, No. 1, pp. 8-11.*
Notice of Opposition by Procter & Gamble, Inc. to EP 1 555 989 (Oct. 15, 2007).
Unilever reply to Opposition to EP 1 555 989 (Mar. 6, 2008).
G.A. Nowak, "*Die kosmetischen Praparate*" Band 2, 1984, pp. 489-495.
Von Horst Fey, "*Worterbuch Der Kosmetik*", 1974, p. 219.
PCT International Search Report in a PCT application PCT/EP 03/10926.

(Continued)

*Primary Examiner*—Yvonne L Eyler
*Assistant Examiner*—Ivan Greene
(74) *Attorney, Agent, or Firm*—Karen E. KLumas

(57) ABSTRACT

A hair and/or scalp treatment composition comprising an amino-oxo-indole-ylidene compound of general formula (I): (I) formula should be here in which: R1, R2, R3 and R4 are each, independently, hydrogen or a monovalent organic group selected from alkyl, alkenyl, alkynyl, aryl, alkylene-aryl, cycloalkyl, cycloalkenyl, and heterocyclyl.

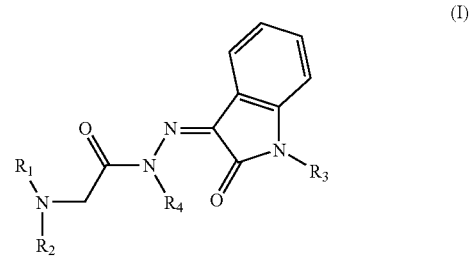

10 Claims, No Drawings

OTHER PUBLICATIONS

PCT International Search Report in a PCT application PCT/EP2006/001823.
PCT International Search Report in a PCT application PCT/EP2006/001683.
PCT International Search Report in a PCT application PCT/EP2006/001824.
ChemDplus Abstract 477-32-7; Visnadine.
Derwent Abstract of JP 62 192313—published Aug. 22, 1987.
Dewent Abstract of 56-061308—published May 26, 1981.
Lejeune et al., "*Propolis Extraits Et Utilsations Dans Des Shampooings Et Lotions*", Parfums, Cosmetiques, Aromes, Societe D; Expansion Technique Et Economique S.A. Paris, Fr., No. 56, Apr. 1984, pp. 65-68.
Knowlton et al., "*Handbook of Cosmetic Science and Technology*",Elsevier Advanced Technology, Aug. 1993, pp. 220-222.
Prakash et al., "*Indian Drugs*", Synthesis and Screening of Potential Biodynamic Agents, vol. 23, Issue 3, 1985.
Co-pending Application: Applicant: Bailey et al., U.S. Appl. No. 10/531,155, filed Sep. 26, 2005.
Co-pending Application: Applicant: Bhogal et al., U.S. Appl. No. 11/886,205, filed Sep. 11, 2007.
Co-pending Application: Applicant: Bhogal et al., U.S. Appl. No. 11/886,206, filed Sep. 11, 2007.
Co-pending Application: Applicant: Bhogal et al., U.S. Appl. No. 11/886,203, filed Sep. 11, 2007.
EP Search Report in EP application EP 09 16 0042.

\* cited by examiner

HAIR AND/OR SCALP CARE COMPOSITIONS INCORPORATING AMINO-OXO-INDOLE-YLIDENE COMPOUNDS

This invention relates to hair and/or scalp care compositions incorporating certain amino-oxo-indole-ylidene compounds. The invention also relates to the use of these amino-oxo-indole-ylidene compounds for the treatment and/or prevention of inflammatory skin conditions such as the scalp skin itching and flaking associated with dandruff.

BACKGROUND

It is widely believed that *Malassezia* yeasts, such as *Malassezia furfur*, are the main cause of dandruff. However, it is unclear why some people suffer from this condition while others do not. What is known is that increasing the level of *Malassezia* on the scalp does not automatically lead to dandruff. This suggests that *Malassezia* is necessary but not sufficient to cause the condition.

Recent studies have demonstrated that dandruff is associated with changes in scalp skin condition. Dandruff scalp skin has been shown to have decreased levels of stratum corneum lipids such as ceramides, an increased susceptibility to application of topical histamine and a perturbed balance in the levels of inflammatory cytokine markers in the stratum corneum. These findings clearly demonstrate that dandruff is associated with changes in scalp skin condition and that dandruff is multifactorial. It is believed that the weakened scalp skin barrier and perturbed condition of the scalp skin renders an individual susceptible to challenge by factors such as *Malassezia*.

The main, if not only, intervention strategy used on the market currently for the treatment of dandruff is the topical application of antifungals such as zinc pyrithione (ZnPTO), octopirox and ketoconazole which are normally delivered from a shampoo. These antifungal agents remove (or at least reduce the level of) the *Malassezia* from the scalp, and provide effective treatment of the dandruff condition.

Although clinically proven to be effective in treating the clinical symptoms of dandruff over a two to four week period, there remains a need to treat the main symptoms of dandruff more effectively and rapidly. The main symptoms of dandruff are visible skin flakes in the hair and on the shoulders and scalp itch. Scalp itch is perceived as being a particular problem in certain parts of the world, for example it is the main symptom of dandruff in China, South-East Asia and India.

As well as treating the clinical signs of dandruff, therefore, there remains a need for providing rapid relief from scalp itch for dandruff sufferers.

WO04/00085 describes how cannabinoid receptor (CBR) activators may be useful in hair treatment compositions for the treatment and/or prevention of symptoms of dandruff such as scalp skin itching and flaking.

The present inventors have found that certain amino-oxo-indole-ylidene compounds are capable of acting as CBR activators, and therefore may be used for the treatment and/or prevention of symptoms of dandruff such as scalp skin itching and flaking.

There is no suggestion in WO04/00085 that these compounds would possess such activity. Their structure is unusual compared to known classes of cannabinoid receptor (CBR) activator, as reviewed for example in Howlett et al., *Pharmacol. Rev.* 54 (2): 161-202, 2002.

SUMMARY OF THE INVENTION

According to the invention there is provided a hair and/or scalp care composition comprising an amino-oxo-indole-ylidene compound of general formula (I):

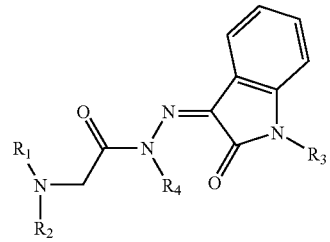

in which:

$R_1$, $R_2$, $R_3$ and $R_4$ are each, independently, hydrogen or a monovalent organic group selected from alkyl, alkenyl, alkynyl, aryl, alkylenearyl, cycloalkyl, cycloalkenyl, and heterocyclyl.

In another aspect, the invention provides a method of treating and/or preventing inflammatory skin conditions such as the scalp skin itching and flaking associated with dandruff, which method comprises topically applying a composition according to the invention to the hair and/or skin, preferably to the hair and/or scalp.

DETAILED DESCRIPTION OF THE INVENTION AND PREFERRED EMBODIMENTS

As used herein, the term "alkyl" includes straight chained and branched saturated hydrocarbon groups, typically methyl, ethyl, and straight chain and branched propyl and butyl groups. The hydrocarbon group can generally contain up to 16 carbon atoms, such as from 1 to 6. The term "alkyl" also includes "bridged alkyl," such as a $C_6$-$C_{16}$ bicyclic or polycyclic hydrocarbon group, for example, norbornyl, adamantyl, bicyclo[2.2.2]octyl, bicyclo[2.2.1]heptyl, bicyclo[3.2.1]octyl, and decahydronaphthyl.

The term "cycloalkyl" is defined as a cyclic saturated hydrocarbon group, typically of 3 to 8 carbon atoms such as cyclopropyl, cyclobutyl, cyclohexyl, or cyclopentyl.

The terms "alkenyl" and "alkynyl" include straight chained and branched unsaturated hydrocarbon groups containing a carbon-carbon double bond or carbon-carbon triple bond, respectively. The hydrocarbon group can generally contain up to 16 carbon atoms, such as from 2 to 6. "Cycloalkenyl" is defined similarly to cycloalkyl, except a carbon-carbon double bond is present in the ring.

The term "alkylene" refers to an alkyl group having a substituent. For example, the term "$C_{1-3}$alkylenearyl" refers to an alkyl group containing one to three carbon atoms, and substituted with an aryl group.

The term "halo" or "halogen" is defined herein to include fluorine, bromine, chlorine, and iodine.

The term "aryl", alone or in combination, is defined herein as a monocyclic or polycyclic aromatic group, preferably a monocyclic or bicyclic aromatic group such as phenyl or naphthyl. An "aryl" group can be unsubstituted or substituted, for example with one or more substituents such as halo, alkyl, hydroxy, hydroxyalkyl, alkoxy, alkoxyalkyl, haloalkyl, haloalkoxy, cyano, nitro, amino, alkylamino, acylamino, thio, alkylthio, alkylsulfinyl, and alkylsulfonyl.

The term "heterocyclyl" is defined herein as a saturated or partially or fully unsaturated monocyclic or bicyclic ring system, containing at least one heteroatom selected from oxygen, nitrogen, or sulphur. A "heterocyclyl" group can be unsubstituted or substituted, for example with one or more substituents such as halo, alkyl, hydroxy, hydroxyalkyl, alkoxy, alkoxyalkyl, haloalkyl, haloalkoxy, cyano, nitro, amino, alkylamino, acylamino, thio, alkylthio, alkylsulfinyl, and alkylsulfonyl. A "heterocyclyl" group can also contain an oxo group (=O) attached to the ring.

$R_1$ and $R_4$ in general formula (I) are preferably independently selected from hydrogen and $C_{1-6}$ alkyl, more preferably from hydrogen and $C_{1-3}$ alkyl. Most preferably $R_1$ and $R_4$ are both hydrogen.

$R_2$ in general formula (I) is preferably an aryl group, more preferably a bicyclic aromatic group. Most preferably $R_2$ is a naphthyl group.

$R_3$ in general formula (I) is preferably an alkylenearyl group, more preferably a $C_{1-3}$alkylenearyl group. Most preferably $R_3$ is a phenethyl ($C_6H_5CH_2CH_2$—) group.

A specific example of an amino-oxo-indole-ylidene compound of general formula (I) is a compound which has the structural formula (II):

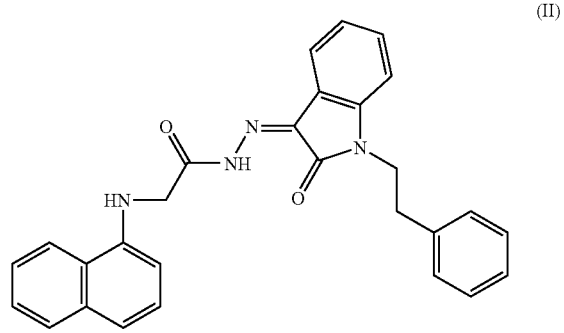

(II)

The above compound of structural formula (II) is termed (naphthalen-1-ylamino)-acetic acid (2-oxo-1-phenethyl-1,2-dihydro-indol-3-ylidene)-hydrazide.

Amino-oxo-indole-ylidene compounds of formula (I) may be obtained from suppliers such as Apin Chemicals Limited (Oxon., UK), Sigma-Aldrich and Interbioscreens.

The amount of amino-oxo-indole-ylidene compound of formula (I) in the compositions of the invention is preferably selected in the range of from 0.05 to 20%, more preferably from 0.1 to 10%, most preferably from 0.25 to 5 wt % by weight based on total weight.

Antidandruff Agent

Preferably, compositions according to the invention comprise from 0.01% to 30% by weight, more preferably 0.1% to 10%, most preferably 0.5 to 2% by weight of an antidandruff agent. By "antidandruff agent" is meant a different compound from the an amino-oxo-indole-ylidene compound of formula (I). Antidandruff agents are compounds that are active against dandruff and are typically antimicrobial agents, preferably antifungal agents.

Suitable antidandruff agents include compounds selected from zinc pyrithione, climbazole, ketoconazole, octopirox and mixtures thereof.

The preferred antifungal agent is zinc pyrithione (ZnPTO) which, on account of its relative insolubility in aqueous systems, is generally used in hair treatment compositions as a particulate dispersion. The zinc pyrithione may be used in any particle form including, for example, crystalline forms such as platelets and needles and amorphous, regularly or irregularly shaped particles. If zinc pyrithione is present in the composition, a suspending agent is preferably used to prevent or inhibit the settling of the particles out of the composition. The average particle diameter of the zinc pyrithione particles (i.e. their maximum dimension) is typically from about 0.2 to about 50 µm, preferably from about 0.4 to about 10 µm, more preferably from 0.4 to 1 µm.

Antifungal agents typically display a minimum inhibitory concentration of about 50 mg/ml or less against *Malassezia*.

If the antifungal agent is soluble in aqueous systems, it may be present in solution in a composition used in the invention.

Product Forms

Compositions of the present invention are typically for topical application to the hair and/or scalp and may be formulated as transparent or opaque emulsions, lotions, creams, pastes or gels.

Hair and/or scalp care compositions of the invention may be rinse off products or leave on products. Rinse off products are intended to be substantially rinsed off the hair and/or the scalp of the user with water after use. Leave on products are intended not to be rinsed off the hair and/or the scalp of the user immediately after use (ie, within at least the first 2 hours, preferably at least four hours, after application of the composition). Leave on products include, for example, lotions, creams and hair oils that are intended for topical application to the hair and/or the scalp. Rinse off compositions include shampoos and hair conditioners, as well as hair and/or scalp treatment products which are intended to be left on the hair and/or scalp for up to 2 hours (eg, 5 minutes to 2 hours) before being rinsed off.

Preferred product forms are shampoos, conditioners, hair oils and lotions.

Shampoo Compositions

Shampoo compositions according to the invention will typically comprise one or more anionic cleansing surfactants which are cosmetically acceptable and suitable for topical application to the hair.

Anionic Cleansing Surfactant

Examples of suitable anionic cleansing surfactants are the alkyl sulphates, alkyl ether sulphates, alkaryl sulphonates, alkanoyl isethionates, alkyl succinates, alkyl sulphosuccinates, N-alkyl sarcosinates, alkyl phosphates, alkyl ether phosphates, alkyl ether carboxylates, and alpha-olefin sulphonates, especially their sodium, magnesium, ammonium and mono-, di- and triethanolamine salts. The alkyl and acyl groups generally contain from 8 to 18 carbon atoms and may be unsaturated. The alkyl ether sulphates, alkyl ether phosphates and alkyl ether carboxylates may contain from 1 to 10 ethylene oxide or propylene oxide units per molecule.

Typical anionic cleansing surfactants for use in shampoo compositions of the invention include sodium oleyl succinate, ammonium lauryl sulphosuccinate, ammonium lauryl sulphate, sodium dodecylbenzene sulphonate, triethanolamine dodecylbenzene sulphonate, sodium cocoyl isethionate, sodium lauryl isethionate and sodium N-lauryl sarcosinate. The most preferred anionic surfactants are sodium lauryl sulphate, sodium lauryl ether sulphate(n)EO, (where n ranges from 1 to 3), ammonium lauryl sulphate and ammonium lauryl ether sulphate(n)EO, (where n ranges from 1 to 3).

Mixtures of any of the foregoing anionic cleansing surfactants may also be suitable.

The total amount of anionic cleansing surfactant in shampoo compositions of the invention is generally from 5 to 30, preferably from 6 to 20, more preferably from 8 to 16 percent by weight of the composition.

Co-Surfactant

Shampoo compositions according to the invention can optionally include co-surfactants, to help impart aesthetic, physical or cleansing properties to the composition.

A preferred example is an amphoteric or zwitterionic surfactant, which can be included in an amount ranging from 0 to about 8, preferably from 1 to 4 wt %.

Examples of amphoteric and zwitterionic surfactants include alkyl amine oxides, alkyl betaines, alkyl amidopropyl betaines, alkyl sulphobetaines (sultaines), alkyl glycinates, alkyl carboxyglycinates, alkyl amphopropionates, alkylamphoglycinates, alkyl amidopropyl hydroxysultaines, acyl taurates and acyl glutamates, wherein the alkyl and acyl groups have from 8 to 19 carbon atoms. Typical amphoteric and zwitterionic surfactants for use in shampoos of the invention include lauryl amine oxide, cocodimethyl sulphopropyl betaine and preferably lauryl betaine, cocamidopropyl betaine and sodium cocamphopropionate.

Another preferred example is a nonionic surfactant, which can be included in an amount ranging from 0 to 8, preferably from 2 to 5 percent by weight of the composition.

For example, representative nonionic surfactants that can be included in shampoo compositions of the invention include condensation products of aliphatic ($C_8$-$C_{18}$) primary or secondary linear or branched chain alcohols or phenols with alkylene oxides, usually ethylene oxide and generally having from 6 to 30 ethylene oxide groups.

Other representative nonionic surfactants include mono- or di-alkyl alkanolamides. Examples include coco mono- or di-ethanolamide and coco mono-isopropanolamide.

Further nonionic surfactants which can be included in shampoo compositions of the invention are the alkyl polyglycosides (APGs). Typically, the APG is one which comprises an alkyl group connected (optionally via a bridging group) to a block of one or more glycosyl groups. Preferred APGs are defined by the following formula:

wherein R is a branched or straight chain alkyl group which may be saturated or unsaturated and G is a saccharide group. R may represent a mean alkyl chain length of from about $C_5$ to about $C_{20}$. Preferably R represents a mean alkyl chain length of from about $C_8$ to about $C_{12}$. Most preferably the value of R lies between about 9.5 and about 10.5. G may be selected from $C_5$ or $C_6$ monosaccharide residues, and is preferably a glucoside. G may be selected from the group comprising glucose, xylose, lactose, fructose, mannose and derivatives thereof. Preferably G is glucose.

The degree of polymerisation, n, may have a value of from about 1 to about 10 or more. Preferably, the value of n lies in the range of from about 1.1 to about 2. Most preferably the value of n lies in the range of from about 1.3 to about 1.5.

Suitable alkyl polyglycosides for use in the invention are commercially available and include for example those materials identified as: Oramix NS10 ex Seppic; Plantaren 1200 and Plantaren 2000 ex Henkel.

Other sugar-derived nonionic surfactants which can be included in shampoo compositions of the invention include the $C_{10}$-$C_{18}$ N-alkyl($C_1$-$C_6$)polyhydroxy fatty acid amides, such as the $C_{12}$-$C_{18}$ N-methyl glucamides, as described for example in WO 92 06154 and U.S. Pat. No. 5,194,639, and the N-alkoxy polyhydroxy fatty acid amides, such as $C_{10}$-$C_{18}$ N-(3-methoxypropyl)glucamide.

A preferred blend of cleansing surfactants is a combination of ammonium lauryl ether sulphate, ammonium lauryl sulphate, PEG 5 cocamide and cocamide MEA (CTFA designations).

The shampoo composition can also optionally include one or more cationic co-surfactants included in an amount ranging from 0.01 to 10, more preferably from 0.05 to 5, most preferably from 0.05 to 2 percent by weight of the composition. Useful cationic surfactants are described hereinbelow in relation to conditioner compositions.

The total amount of surfactant (including any co-surfactant, and/or any emulsifier) in shampoo compositions of the invention is generally from 5 to 50, preferably from 5 to 30, more preferably from 10 to 25 percent by weight of the composition.

Cationic Polymer

A cationic polymer is a preferred ingredient in shampoo compositions according to the invention, for enhancing conditioning performance of the shampoo.

The cationic polymer may be a homopolymer or be formed from two or more types of monomers. The molecular weight of the polymer will generally be between 5 000 and 10 000 000, typically at least 10 000 and preferably in the range 100 000 to about 2 000 000. The polymers will have cationic nitrogen containing groups such as quaternary ammonium or protonated amino groups, or a mixture thereof.

The cationic nitrogen-containing group will generally be present as a substituent on a fraction of the total monomer units of the cationic polymer. Thus when the polymer is not a homopolymer it can contain spacer non-cationic monomer units. Such polymers are described in the CTFA Cosmetic Ingredient Directory, 3rd edition. The ratio of the cationic to non-cationic monomer units is selected to give a polymer having a cationic charge density in the required range.

Suitable cationic conditioning polymers include, for example, copolymers of vinyl monomers having cationic amine or quaternary ammonium functionalities with water soluble spacer monomers such as (meth)acrylamide, alkyl and dialkyl(meth)acrylamides, alkyl(meth)acrylate, vinyl caprolactone and vinyl pyrrolidine. The alkyl and dialkyl substituted monomers preferably have C1-C7 alkyl groups, more preferably C1-3 alkyl groups. Other suitable spacers include vinyl esters, vinyl alcohol, maleic anhydride, propylene glycol and ethylene glycol.

The cationic amines can be primary, secondary or tertiary amines, depending upon the particular species and the pH of the composition. In general secondary and tertiary amines, especially tertiary, are preferred.

Amine substituted vinyl monomers and amines can be polymerized in the amine form and then converted to ammonium by quaternization.

The cationic conditioning polymers can comprise mixtures of monomer units derived from amine- and/or quaternary ammonium-substituted monomer and/or compatible spacer monomers.

Suitable cationic conditioning polymers include, for example:
copolymers of 1-vinyl-2-pyrrolidine and 1-vinyl-3-methyl-imidazolium salt (e.g. chloride salt), referred to in the industry by the Cosmetic, Toiletry, and Fragrance Association, (CTFA) as Polyquaternium-16. This material is commercially available from BASF Wyandotte Corp. (Parsippany, N.J., USA) under the LUVIQUAT tradename (e.g. LUVIQUAT FC 370);

copolymers of 1-vinyl-2-pyrrolidine and dimethylaminoethyl methacrylate, referred to in the industry (CTFA) as Polyquaternium-11. This material is available commercially from Gaf Corporation (Wayne, N.J., USA) under the GAFQUAT tradename (e.g., GAFQUAT 755N);

cationic diallyl quaternary ammonium-containing polymers including, for example, dimethyldiallylammonium chloride homopolymer and copolymers of acrylamide and dimethyldiallylammonium chloride, referred to in the industry (CTFA) as Polyquaternium 6 and Polyquaternium 7, respectively;

mineral acid salts of amino-alkyl esters of homo- and copolymers of unsaturated carboxylic acids having from 3 to 5 carbon atoms, (as described in U.S. Pat. No. 4,009,256);

cationic polyacrylamides (as described in WO95/22311).

Other cationic conditioning polymers that can be used include cationic polysaccharide polymers, such as cationic cellulose derivatives, cationic starch derivatives, and cationic guar gum derivatives. Suitably, such cationic polysaccharide polymers have a charge density in the range from 0.1 to 4 meq/g.

Cationic polysaccharide polymers suitable for use in compositions of the invention include those of the formula:

$$A\text{-}O\text{---}[R\text{---}N^+(R^1)(R^2)(R^3)X^-],$$

wherein: A is an anhydroglucose residual group, such as a starch or cellulose anhydroglucose residual. R is an alkylene, oxyalkylene, polyoxyalkylene, or hydroxyalkylene group, or combination thereof. $R^1$, $R^2$ and $R^3$ independently represent alkyl, aryl, alkylaryl, arylalkyl, alkoxyalkyl, or alkoxyaryl groups, each group containing up to about 18 carbon atoms. The total number of carbon atoms for each cationic moiety (i.e., the sum of carbon atoms in $R^1$, $R^2$ and $R^3$) is preferably about 20 or less, and X is an anionic counterion.

Cationic cellulose is available from Amerchol Corp. (Edison, N.J., USA) in their Polymer JR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200.

Other suitable cationic polysaccharide polymers include quaternary nitrogen-containing cellulose ethers (e.g. as described in U.S. Pat. No. 3,962,418), and copolymers of etherified cellulose and starch (e.g. as described in U.S. Pat. No. 3,958,581).

A particularly suitable type of cationic polysaccharide polymer that can be used is a cationic guar gum derivative, such as guar hydroxypropyltrimonium chloride (commercially available from Rhone-Poulenc in their JAGUAR trademark series).

Examples are JAGUAR C13S, which has a low degree of substitution of the cationic groups and high viscosity. JAGUAR C15, having a moderate degree of substitution and a low viscosity, JAGUAR C17 (high degree of substitution, high viscosity), JAGUAR C16, which is a hydroxypropylated cationic guar derivative containing a low level of substituent groups as well as cationic quaternary ammonium groups, and JAGUAR 162 which is a high transparency, medium viscosity guar having a low degree of substitution.

Preferably the cationic conditioning polymer is selected from cationic cellulose and cationic guar derivatives.

Particularly preferred cationic polymers are JAGUAR C13S, JAGUAR C15, JAGUAR C17 and JAGUAR C16 and JAGUAR C162.

The cationic conditioning polymer will generally be present in compositions of the invention at levels of from 0.01 to 5, preferably from 0.05 to 1, more preferably from 0.08 to 0.5 percent by weight of the composition.

When cationic conditioning polymer is present in a shampoo composition according to the invention, it is preferred if the copolymer is present as emulsion particles with a mean diameter ($D_{3,2}$ as measured by light scattering using a Malvern particle sizer) of 2 micrometres or less.

Hair Conditioner Compositions

Compositions in accordance with the invention may also be formulated as conditioners for the treatment of hair (typically after shampooing) and subsequent rinsing.

Hair conditioner compositions according to the invention will suitably comprise a cationic conditioning surfactant that is cosmetically acceptable and suitable for topical application to the hair.

Cationic Conditioning Surfactant

Examples of suitable cationic conditioning surfactants are those corresponding to the general formula:

$$[N(R_1)(R_2)(R_3)(R_4)]^+(X)^-$$

in which $R_1$, $R_2$, $R_3$, and $R_4$ are independently selected from (a) an aliphatic group of from 1 to 22 carbon atoms, or (b) an aromatic, alkoxy, polyoxyalkylene, alkylamido, hydroxyalkyl, aryl or alkylaryl group having up to 22 carbon atoms; and X is a salt-forming anion such as those selected from halogen, (e.g. chloride, bromide), acetate, citrate, lactate, glycolate, phosphate nitrate, sulphate, and alkylsulphate radicals.

The aliphatic groups can contain, in addition to carbon and hydrogen atoms, ether linkages, and other groups such as amino groups. The longer chain aliphatic groups, e.g., those of about 12 carbons, or higher, can be saturated or unsaturated.

Preferred cationic conditionings surfactants are monoalkyl quaternary ammonium compounds in which the alkyl chain length is C16 to C22.

Other preferred cationic conditioning surfactants are so-called dialkyl quaternary ammonium compounds in which R1 and R2 independently have an alkyl chain lengths from C16 to C22 and R3 and R4 have 2 or less carbon atoms.

Examples of suitable cationic surfactants include: cetyltrimethylammonium chloride, behenyltrimethylammonium chloride, cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, cocotrimethylammonium chloride, PEG-2 oleylammonium chloride and salts of these where the chloride is replaced by halogen, (e.g., bromide), acetate, citrate, lactate, glycolate, phosphate nitrate, sulphate, or alkylsulphate. Further suitable cationic surfactants include those materials having the CTFA designations Quaternium-5, Quaternium-31 and Quaternium-18. Mixtures of any of the foregoing materials may also be suitable. A particularly useful cationic conditioning surfactant is cetyltrimethylammonium chloride, available commercially, for example as GENAMIN CTAC, ex Hoechst Celanese.

Salts of primary, secondary, and tertiary fatty amines are also suitable cationic conditioning surfactants. The alkyl groups of such amines preferably have from about 12 to about 22 carbon atoms, and can be substituted or unsubstituted.

Particularly useful are amido substituted tertiary fatty amines. Such amines, useful herein, include stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, diethylaminoethylstearamide. Also useful are dimethylstearamine, dimethylsoyamine, soyamine, myristylamine, tridecylamine, ethylstearylamine, N-tallowpropane diamine, ethoxylated (with 5 moles of ethylene oxide) stearylamine, dihydroxyethylstearylamine, and arachidyl behenylamine. These amines are typically used in combination with an acid to provide the cationic species. The preferred acid useful herein includes L-glutamic acid, lactic acid, hydrochloric acid, malic acid, succinic acid, acetic acid, fumaric acid, tartaric acid, citric acid, L-glutamic hydrochloride, and mixtures thereof; more preferably L-glutamic acid, lactic acid, citric acid. Cationic amine surfactants included among those useful in the present invention are disclosed in U.S. Pat. No. 4,275,055 to Nachtigal, et al., issued Jun. 23, 1981.

The molar ratio of protonatable amines to $H^+$ from the acid is preferably from about 1:0.3 to 1:1.2, and more preferably from about 1:0.5 to about 1:1.1.

In the conditioners of the invention, the level of cationic conditioning surfactant is suitably from 0.01 to 10, preferably from 0.05 to 5, more preferably from 0.1 to 2 percent by weight of the total composition.

Fatty Materials

Hair conditioner compositions according to the invention preferably additionally comprise fatty materials.

By "fatty material" is meant a fatty alcohol, an alkoxylated fatty alcohol, a fatty acid or a mixture thereof.

Preferably, the alkyl chain of the fatty material is fully saturated.

Representative fatty materials comprise from 8 to 22 carbon atoms, more preferably 16 to 22. Preferred fatty materials include cetyl alcohol, stearyl alcohol and mixtures thereof.

Alkoxylated, (e.g. ethoxylated or propoxylated) fatty alcohols having from about 12 to about 18 carbon atoms in the alkyl chain can be used in place of, or in addition to, the fatty alcohols themselves. Suitable examples include ethylene glycol cetyl ether, polyoxyethylene (2) stearyl ether, polyoxyethylene (4) cetyl ether, and mixtures thereof.

The level of fatty material in conditioners of the invention is suitably from 0.01 to 15, preferably from 0.1 to 10, and more preferably from 0.1 to 5 percent by weight of the composition. The weight ratio of cationic surfactant to fatty material is suitably from 10:1 to 1:10, preferably from 4:1 to 1:8, optimally from 1:1 to 1:7, for example 1:3.

Hair conditioner compositions of the invention can also contain a cationic polymer. Suitable cationic polymers are described hereinabove in relation to shampoo compositions.

Hair Oils and Lotions

Hair oils are also suitable product forms according to the invention. Hair oils predominantly comprise water-insoluble oily conditioning materials. Lotions are aqueous emulsions comprising water-insoluble oily conditioning materials. Suitable surfactants can also be included in lotions to improve their stability to phase separation.

Other Optional Ingredients

Compositions of this invention may contain any other ingredient normally used in hair treatment formulations.

Suspending Agents

Hair treatment compositions according to the invention such as shampoos suitably comprise from 0.1 to 5 wt % of a suspending agent. Suitable suspending agents are selected from polyacrylic acids, cross-linked polymers of acrylic acid, copolymers of acrylic acid with a hydrophobic monomer, copolymers of carboxylic acid-containing monomers and acrylic esters, cross-linked copolymers of acrylic acid and acrylate esters, heteropolysaccharide gums and crystalline long chain acyl derivatives. The long chain acyl derivative is desirably selected from ethylene glycol stearate, alkanolamides of fatty acids having from 16 to 22 carbon atoms and mixtures thereof. Ethylene glycol distearate and polyethylene glycol 3 distearate are preferred long chain acyl derivatives. Polyacrylic acid is available commercially as Carbopol 420, Carbopol 488 or Carbopol 493. Polymers of acrylic acid cross-linked with a polyfunctional agent may also be used, they are available commercially as Carbopol 910, Carbopol 934, Carbopol 940, Carbopol 941 and Carbopol 980. An example of a suitable copolymer of a carboxylic acid containing a monomer and acrylic acid esters is Carbopol 1342. All Carbopol (trade mark) materials are available from Goodrich.

Suitable cross-linked polymers of acrylic acid and acrylate esters are Pemulen TR1 or Pemulen TR2. A suitable heteropolysaccharide gum is xanthan gum, for example that available as Kelzan mu.

Further Conditioning Agents

Hair treatment compositions according to the invention such as shampoos and conditioners suitably contain further conditioning agents such as silicone conditioning agents and non-silicone oily conditioning agents.

Suitable silicone conditioning agents include polydiorganosiloxanes, in particular polydimethylsiloxanes which have the CTFA designation dimethicone. Also suitable for use in compositions of the invention (particularly shampoos and conditioners) are polydimethyl siloxanes having hydroxyl end groups, which have the CTFA designation dimethiconol. Also suitable for use in compositions of the invention are silicone gums having a slight degree of cross-linking, as are described for example in WO 96/31188. These materials can impart body, volume and stylability to hair, as well as good wet and dry conditioning. Also suitable are functionalised silicones, particularly amino-functionalised silicones.

Suitable non-silicone oily conditioning agents are selected from hydrocarbon oils, fatty esters and mixtures thereof.

The further conditioning agent is suitably present in shampoo or conditioner compositions at a level of from 0.05 to 10, preferably from 0.2 to 5, more preferably from about 0.5 to 3 percent by total weight of further conditioning agent based on total weight of the composition.

Hair treatment compositions of the invention may contain other optional ingredients for enhancing performance and/or consumer acceptability, such as fragrance, dyes and pigments, pH adjusting agents, pearlescers or opacifiers, viscosity modifiers, preservatives, and natural hair nutrients such as botanicals, fruit extracts, sugar derivatives and amino acids.

The invention is further illustrated with reference to the following, non-limiting examples, in which all percentages are by weight based on total weight unless otherwise specified.

EXAMPLES

Example 1

An amino-oxo-indole-ylidene compound of formula (I) was evaluated for its ability to activate Cannabinoid Receptor 1 (CB1R) and Cannabinoid Receptor 2 (CB2R). Its C log P value were also measured.

CB1R experiments were performed using membranes from HEK293 cells over-expressing human recombinant $CB_1$, as described by the manufacturer (Perkin-Elmer) and using [3H]CP-55,490 as the radioligand.

CB2R experiments were performed using membranes from HEK293 cells over-expressing human recombinant $CB_2$, as described by the manufacturer (Perkin-Elmer), and using [3H]CP-55,495 as the radioligand.

Data of the active compound is expressed in $K_i$ (mM) and are means±SEM of n=3 determinations.

The value stated is an EC50 value. This is defined as the molar concentration of an agonist, which produces 50% of the maximum possible response for that agonist. The values documented are in micromolar units.

The absence of a value in the table indicates that greater than 25 micromolar concentration was required for 50% binding of the ligand to the receptor.

Also, the C log P values of the compound was calculated using SYBYL v6.8 (Tripos Inc., Missouri).

The results are shown in the following Table:

| Example | Compound | CB1R Activity | CB2R Activity | ClogP |
|---------|----------|---------------|---------------|-------|
| 1 | (Naphthalen-1-ylamino)-acetic acid (2-oxo-1-phenethyl-1,2-dihydro-indol-3-ylidene)-hydrazide | — | 21.10 | 6.25 |

Example 2

The following is an example of a shampoo composition according to the invention:

| Ingredient Chemical Name | Example 2 a.i. weight % |
|---|---|
| SLES 2EO | 14 |
| Cocoamidopropylbetaine | 2 |
| Guar hydroxypropyltrimonium chloride | 0.1 |
| Dimethiconol | 1 |
| Crosslinked polyacrylic acid | 0.4 |
| Zinc pyrithione | 0.5 |

-continued

| Ingredient Chemical Name | Example 2 a.i. weight % |
|---|---|
| (Naphthalen-1-ylamino)-acetic acid (2-oxo-1-phenethyl-1,2-dihydro-indol-3-ylidene)-hydrazide | 0.6 |
| Mica + titanium dioxide | 0.2 |
| Sodium benzoate | 0.5 |
| Water | to 100 |

The invention claimed is:

1. An antidandruff hair and/or scalp care composition comprising an effective amount of an amino-oxo-indole-ylidiene compound of the general formula (I):

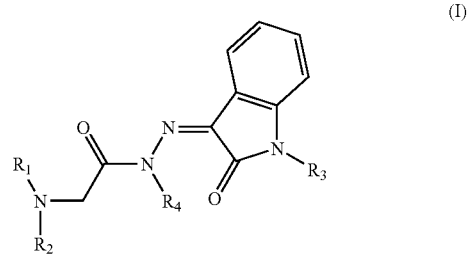

in which $R_1$ and $R_4$ are independently selected from hydrogen and $C_{1-6}$ alkyl, $R_2$ is a bicyclic aromatic group, and $R_3$ is an alkylenearyl group.

2. A composition according to claim 1 characterised in that the amino-oxo-indole-ylidene compound of general formula (I) is naphthalen-1-ylamino)-acetic acid (2-oxo-1-phenethyl-1,2-dihydro-indol-3-ylidene)-hydrazide.

3. A composition according to claim 1 characterised in that it comprises from 0.01 to 30% by weight of an antidandruff agent.

4. A composition according to claim 3 characterised in that the antidandruff agent comprises a compound selected from zinc pyrithione, climbazole, ketoconazole, octopirox and mixtures thereof.

5. A composition according to claim 1 characterised in that it is a shampoo composition comprising an anionic cleansing surfactant in an amount of from 5 to 30 wt %.

6. A composition according to claim 1 characterised in that it is a conditioner composition comprising a cationic conditioning surfactant in an amount of from 0.01 to 10 wt %.

7. A composition according to claim 1 characterised in that it is a hair oil or lotion.

8. A composition according to claim 1 characterised in that the amount of the amino-oxo-indole-ylidene compound of general formula (I) is from 0.05 to 20% by weight.

9. A method of treating and/or preventing the scalp skin itching and flaking associated with dandruff, said method comprising topically applying a composition according to claim 1 to the hair and/or scalp.

10. A composition according to claim 1 wherein the amount of the amino-oxo-indole-ylidene compound of general formula (I) is from 0.1 to 10% by weight.

* * * * *